United States Patent

Miller

[11] Patent Number: 5,853,380
[45] Date of Patent: Dec. 29, 1998

[54] SOFT ANKLE/FOOT ORTHOSIS

[75] Inventor: John J. Miller, Easton, Mass.

[73] Assignee: Boston Brace International Inc., Avon, Mass.

[21] Appl. No.: 898,016

[22] Filed: Jul. 22, 1997

Related U.S. Application Data

[63] Continuation of Ser. No. 587,252, Jan. 16, 1996, abandoned, which is a continuation of Ser. No. 190,342, Feb. 2, 1994, abandoned.

[51] Int. Cl.[6] .................................................. A61F 5/00
[52] U.S. Cl. ............................................... 602/27; 602/23
[58] Field of Search ................................... 602/5, 19, 23, 602/27–29; 128/882, 892

[56] References Cited

U.S. PATENT DOCUMENTS

| | | | |
|---|---|---|---|
| 3,871,367 | 3/1975 | Miller | 602/19 |
| 4,186,738 | 2/1980 | Schleicher et al. | 602/23 X |
| 4,494,536 | 1/1985 | Latenser | 128/882 |
| 4,693,239 | 9/1987 | Clover, Jr. | 602/27 |
| 4,771,768 | 9/1988 | Crispin | 602/27 X |
| 5,020,523 | 6/1991 | Bodine | 602/27 |
| 5,072,725 | 12/1991 | Miller | 602/19 |
| 5,074,288 | 12/1991 | Miller | 602/19 |
| 5,226,245 | 7/1993 | Lamont | 128/892 X |

Primary Examiner—Linda C. M. Dvorak
Attorney, Agent, or Firm—Kriegsman & Kriegsman

[57] ABSTRACT

A soft ankle/foot orthosis for protecting the ankle and foot of a person. In a preferred embodiment, the soft ankle/foot orthosis comprises an outer layer of soft compressible plastic material and an inner layer of soft compressible plastic material. The inner layer of soft compressible plastic material is bonded to the inside of the outer layer of soft compressible plastic material, the inner layer and the outer layer together defining a split shell. The shell is sized and has a molded shape corresponding generally to the lower leg and foot of the person on whom it is to be worn, the lower leg portion and the foot portion of the shell being oriented generally perpendicular to one another to properly position the ankle so as to prevent fractures to the foot and/or ankle. To protect an ulcerative heel and/or ulcerative toes from contact with potentially irritating items, the shell is enlarged in the back and bottom of the heel region and is sized to extend beyond the toes of the person. One or more reinforcing stays are fixedly sandwiched between the inner layer and the outer layer to assist in holding the shell in its molded shape. A plurality of releasable fasteners are used to hold the shell in place on the wearer.

7 Claims, 6 Drawing Sheets

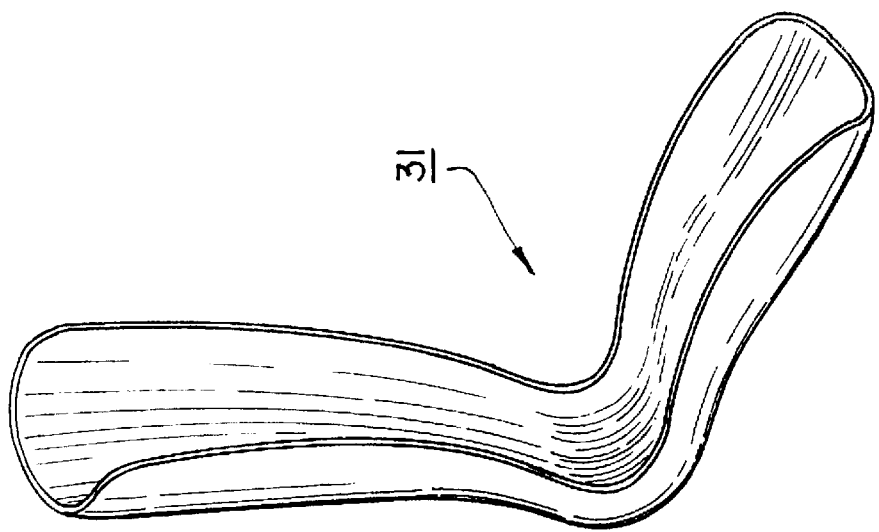
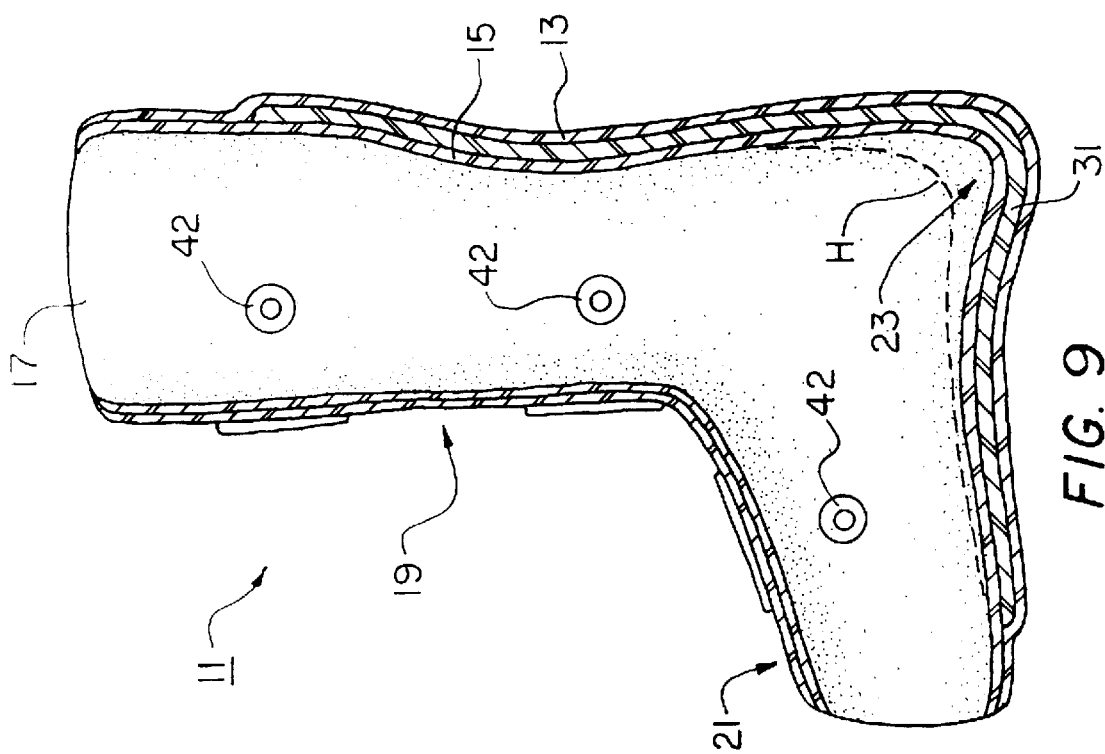

SOFT ANKLE/FOOT ORTHOSIS

This application is a continuation of application 08/587,252 filed on Jan. 16, 1996, now abandoned, which is in turn a continuation of U.S. Ser. No. 08/190,342, filed Feb. 2, 1994, now abandoned.

BACKGROUND OF THE INVENTION

The present invention relates generally to ankle/foot orthoses and more particularly to a new ankle/foot orthosis.

Ankle/foot orthoses constitute a well-known class of orthoses in the art and are typically worn by patients suffering from one or both of the following conditions: (1) Where, for example, the patient has a foot that angles downwardly (as opposed to being generally perpendicular to the patient's lower leg), an ankle/foot orthosis is commonly used to keep the patient's foot generally perpendicular to his/her lower leg, thereby protecting the patient's ankle and/or foot from fracture; and (2) Where, for example, the patient has ulcers on his/her heel and/or toes, an ankle/foot orthosis is often used to protect the patient's heel and/or toes from contact with bedsheets or other items that have a tendency to rub against the ulcers and aggravate them.

One common type of ankle/foot orthosis, which is designed to address only the aforementioned problem of keeping the foot generally perpendicular to the lower leg, is shaped similar to a boot and comprises an outer layer of a hard plastic material and an inner layer of a soft foam material. Because of its rigidity and strength in construction, this type of ankle/foot orthosis may be used for long-term ambulation.

Another common type of ankle/foot orthosis, which is designed to address both the problem of keeping the foot generally perpendicular to the lower leg and of protecting ulcerative heels and toes, is commonly referred to in the art as a multipodus splint. A multipodus splint typically comprises a soft, flexible, sock-like element and a hard supporting element secured to the sock-like element. The sock-like element, which is typically lined with sheepskin, has an open toe and an open heel to minimize contact with ulcers formed on the heel and toes. The support element is shaped to extend along the back of the leg and the bottom of the foot in a generally perpendicular manner. The heel portion of the support is curved so as to bend both away from the leg and down from the foot to shield the heel of the wearer from contact with items that may aggravate heel ulcers. The splint may further include a toe plate adjustably mounted on the bottom of the support which extends to a desired length out beyond the toes of the wearer in such a manner as to prevent bedsheets or the like from contacting the toes.

Multipodus splints of the type described above are typically not intended for long-term ambulation without a cast boot, but rather, are primarily intended for sleeping and nighttime use.

Unfortunately, many of the patients who use multipodus splints of the type described above are incontinent. As can readily be appreciated, because the sock-like material of the splint is made of sheepskin, it difficult to maintain the cleanliness of the splint for incontinent patients.

Patents of interest include U.S. Pat. Nos. 5,074,288, 5,072,725 and 3,871,367, all of which are incorporated herein by reference. In U.S. Pat. No. 5,074,288, which issued Dec. 24, 1991 to Miller, there is disclosed a soft body brace which may be used for providing support for non-structural deformities caused by muscle imbalance and weakness, the brace comprising an outer layer of soft compressible plastic material and an inner layer of soft compressible plastic material, the inner layer being bonded to the outer layer of soft compressible plastic material. The inner and outer layers together define a shell sized and configured to circumscribe the trunk of a person and having a top edge and a bottom edge, a posterior portion and a vertically split anterior portion. A plurality of transversely spaced vertically disposed reinforcing stays are fixedly sandwiched between the outer and inner layers for maintaining the shell in the desired shape. Curved pads are also sandwiched between the inner and outer layers for engaging the iliac crests of the wearer. Releasable fasteners are attached to the open anterior ends of the shell to aid in securing the shell on the wearer.

In U.S. Pat. No. 5,072,725, which issued Dec. 17, 1991 to Miller, there is disclosed a soft body brace for providing support for certain types of patients includes an inner layer of soft compressible plastic material and an outer layer of soft compressible plastic material, the outer layer of soft compressible plastic material being bonded to the inner layer of soft compressible plastic material and along with the inner layer defining a shell configured to circumscribe the torso of the wearer and having a split portion. A plurality of sleeves of flexible material are sandwiched between the inner and outer layers and a reinforcing stay is fixedly disposed in each sleeve for maintaining the brace in its intended shape. Releasable fasteners are attached to the split portion for maintaining the brace in place on the wearer. In making the soft body brace, the shell is first fabricated and then shaped as necessary to conform to the shape of the intended wearer. Reinforcing stays are then cut to size bent as needed to conform to the shape of the wearer at their intended locations and inserted into the respective sleeves. The ends of the sleeves are then sealed off to prevent removal of the reinforcing stays. The fastener assemblies are then attached to the split portion of the shell.

In U.S. Pat. No. 3,871,367, which issued Mar. 18, 1975 to Miller, there is disclosed a pelvic girdle comprising an outer layer of a hard substantially rigid plastic material and an inner layer of soft compressible plastic material bonded to the outer layer, the girdle being shaped to engage a person's pelvis and including an interior and a vertically split posterior portion, the girdle having an upper anterior portion separated laterally from the remainder of the girdle and curving outwardly thereof, and connecting upper side portions on the girdle connecting the anterior and posterior portions thereof and including inwardly curved sections in both layers of the girdle for engaging the iliac crests of the wearer and which sections have appreciably thicker compressible inner layers thereon.

SUMMARY OF THE INVENTION

It is an object of the present invention to provide a new ankle/foot orthosis.

It is another object of the present invention to provide an ankle/foot orthosis that, like a multipodus splint, can be used both to properly position a foot and to protect ulcerative heels and toes but that is easier to maintain in a hygienic condition for use by incontinent patients than is typically the case with multipodus splints.

It is still another object of the present invention to provide an ankle/foot that is simple in construction and inexpensive to manufacture.

It is still yet another object of the present invention to provide an ankle/foot orthosis that is lightweight and comfortable enough to wear in bed.

Additional objects, as well as features and advantages thereof, will be set forth in part in the description which follows, and in part will be obvious from the description or may be learned by practice of the invention. The objects of the invention also may be realized and attained by means of instrumentalities and combinations particularly pointed out in the appended claims.

In accordance with a preferred embodiment of the invention, a soft ankle/foot orthosis for protecting the ankle and foot of a person is provided herein, the soft ankle/foot orthosis comprising an outer layer of soft compressible plastic material and an inner layer of soft compressible plastic material. The inner layer of soft compressible plastic material is bonded to the inside of the outer layer of soft compressible plastic material, the inner layer and the outer layer together defining a split shell. The shell is sized and has a molded shape corresponding generally to the lower leg and foot of the person on whom it is to be worn, the lower leg portion and the foot portion of the shell being oriented generally perpendicular to one another to properly position the ankle so as to prevent fractures to the foot and/or ankle. To protect an ulcerative heel and/or ulcerative toes from contact with potentially irritating items, the shell is enlarged in the back and bottom of the heel region and is sized to extend beyond the toes of the person. One or more reinforcing stays are fixedly sandwiched between the inner layer and the outer layer to assist in holding the shell in its molded shape. A plurality of releasable fasteners are used to hold the shell in place on the wearer.

The above-described soft ankle/foot orthosis is particularly well-suited for nighttime and bed use and is not primarily intended for long-term ambulation without a cast boot.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In the drawings wherein like reference numerals represent like parts:

FIG. 9 is a section view of the ankle/foot orthosis of FIG. 1 taken along line 8—8 of FIG. 5, the dotted lines representing in phantom the heel of a person wearing the ankle/foot orthosis;

FIG. 12 is a front, left, top perspective view of the reinforcing stay used in the ankle/foot orthosis of FIG. 1.

DETAILED DESCRIPTION OF PREFERRED EMBODIMENTS

Figure 2:
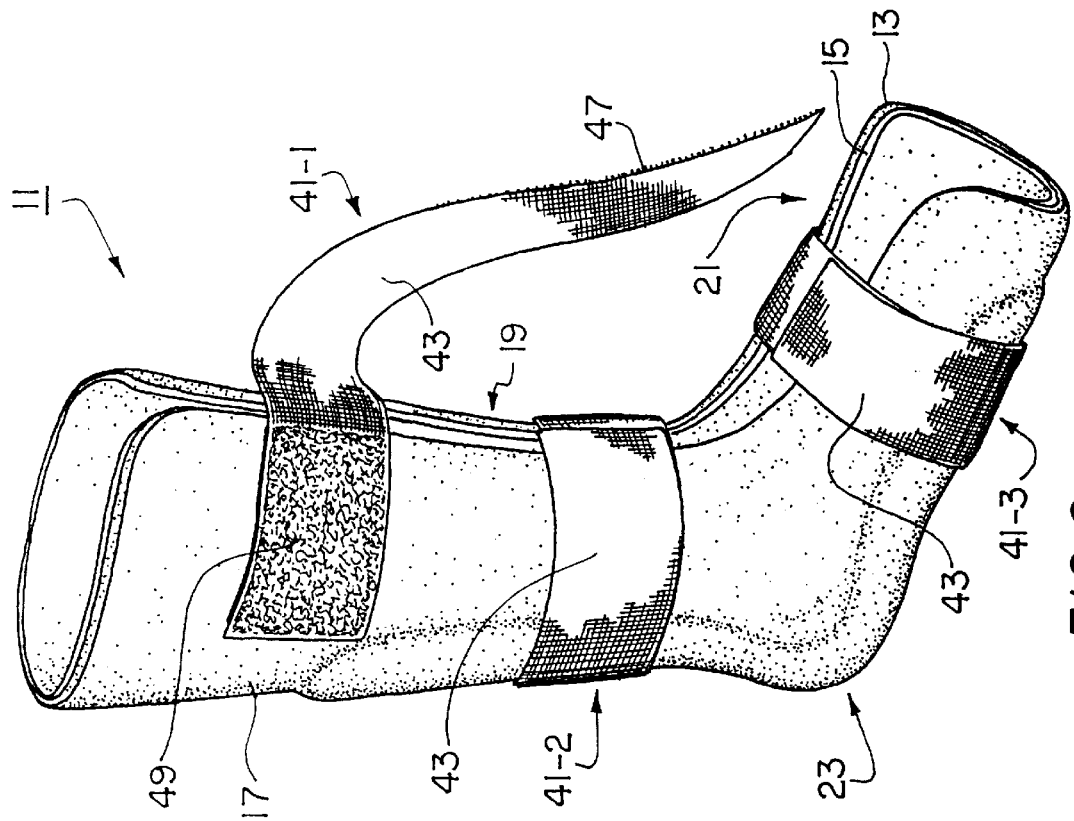
FIG. 2 is a front, left, top perspective view of the ankle/foot orthosis shown in FIG. 1, one of the fasteners of the ankle/foot orthosis being shown in the open position.
Figure 1:
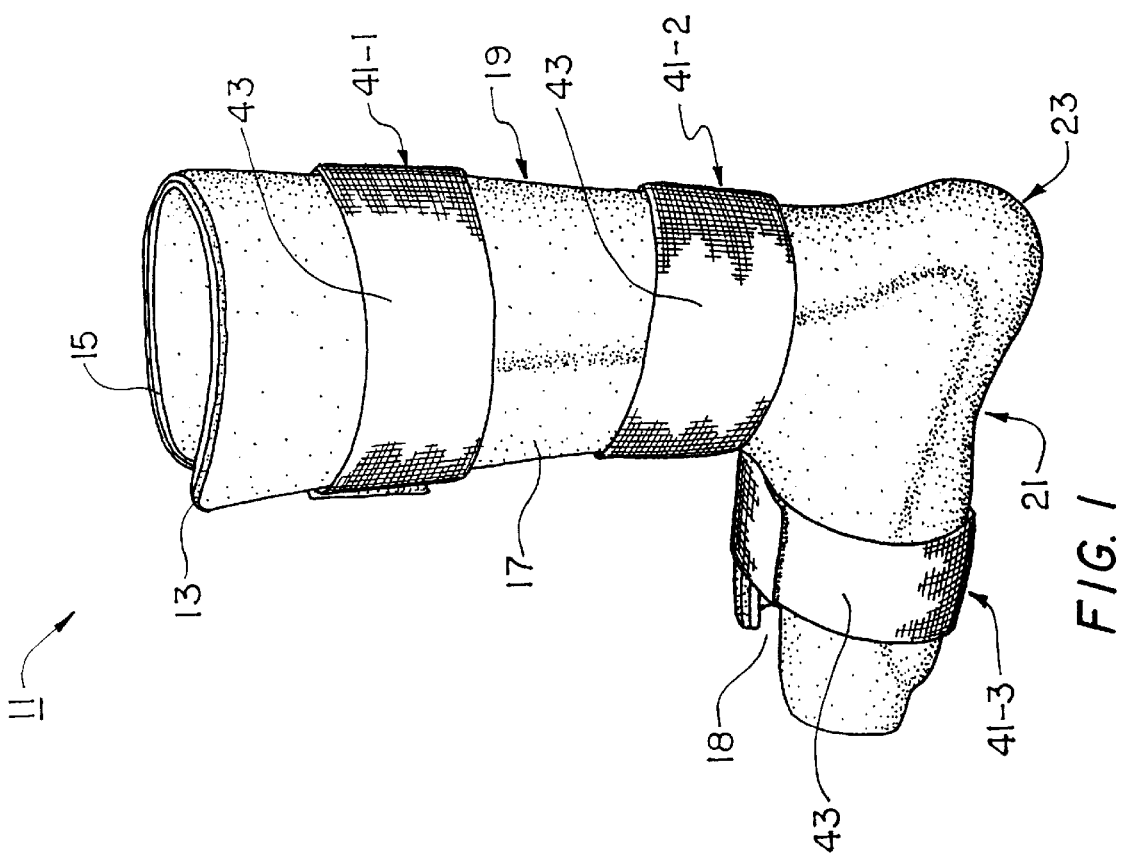
FIG. 1 is a rear, right, top perspective view of one embodiment of a soft ankle/foot orthosis constructed according to the teachings of the present invention.
Figure 4:
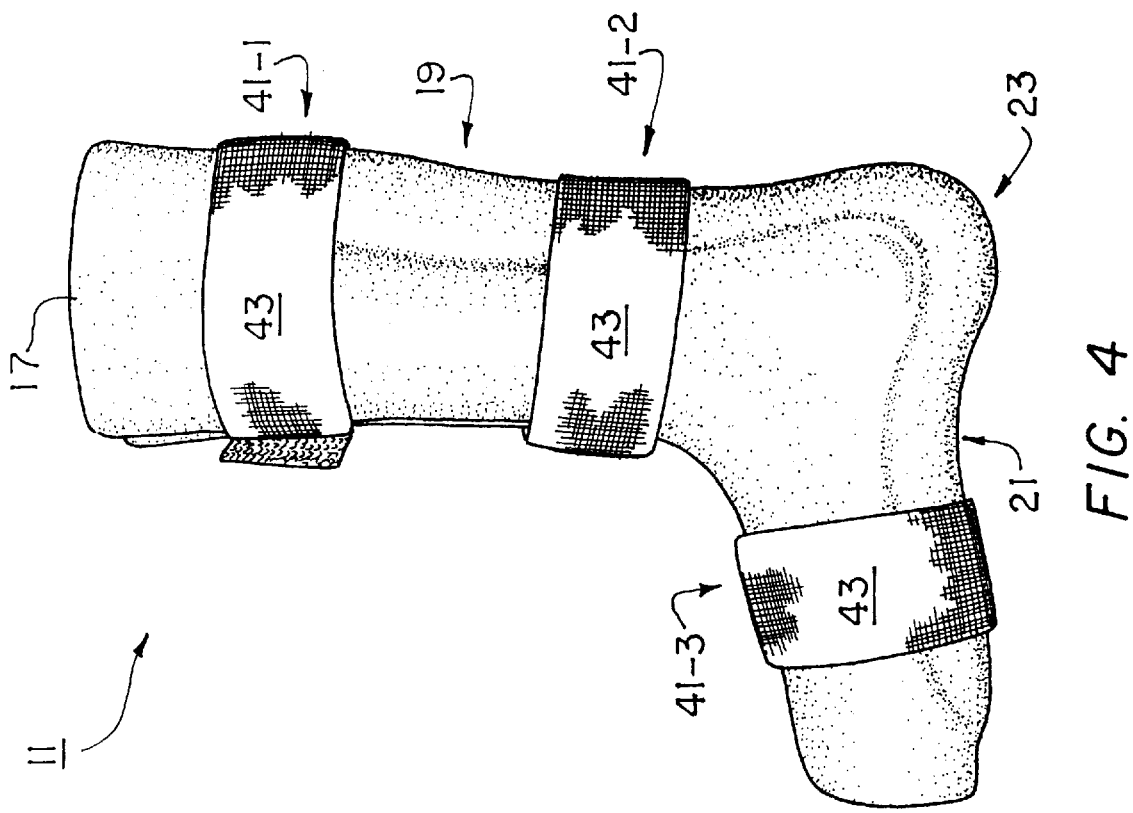
FIG. 4 is a right side view of the ankle/foot orthosis shown in FIG. 1.
Figure 3:
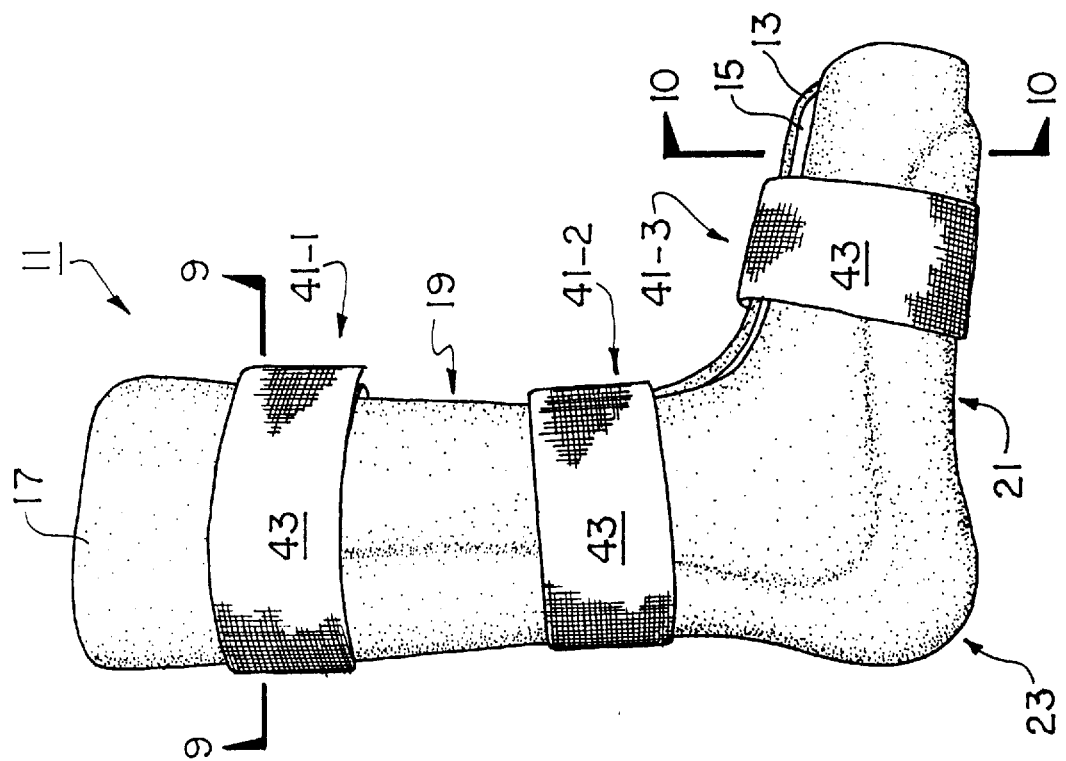
FIG. 3 is a left side view of the ankle/foot orthosis shown in FIG. 1.
Figure 6:
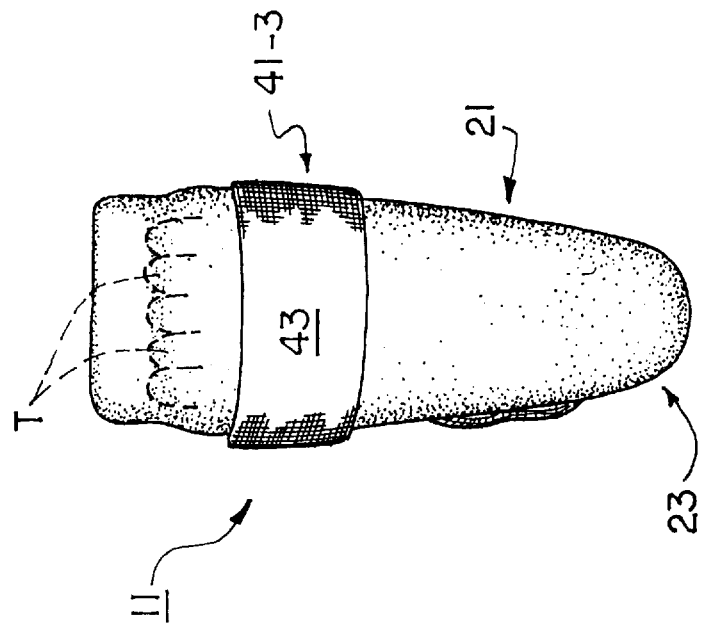
FIG. 6 is a bottom view of the ankle/foot orthosis shown in FIG. 1, the dotted lines representing in phantom the toes of a person wearing the ankle/foot orthosis.

The present invention is directed to a soft ankle/foot orthosis which is designed (1) to maintain a wearer's foot and lower leg in a generally perpendicular orientation relative to one another to prevent fractures of the wearer's ankle and/or foot; and (2) to shield a wearer's heel and toes from contact with ulcer-aggravating materials.

Referring now to FIGS. 1 through 11, there are shown various views of one embodiment of a soft ankle/foot orthosis constructed according to the teachings of the present invention, the soft ankle/foot orthosis being represented by reference numeral 11.

Orthosis 11, which is sized and shaped to fit over a patient's lower leg and foot, comprises an outer layer 13 of soft compressible plastic material and an inner layer 15 of soft compressible plastic material. Layers 13 and 15 are each approximately ¼ inch in thickness, with layer 15 being, for example, a closed cell polyethylene foam, such as a VOLARA Type EO Aliplast and layer 13 being, for example, a slightly more rigid closed cell polyethylene foam, such as PLASTAZOTE LD45. Layer 13 is bonded to layer 15 by heat as will hereinafter be described. In addition, a suitable adhesive (not shown) may be used to enhance the bonding.

Outer layer 13 and inner layer 15 together define a shell 17 having a leg portion 19 and a foot portion 21, leg portion 19 and foot portion 21 being oriented generally perpendicularly to one another (see FIGS. 3 and 4) so that the wearer's ankle and foot are protected against fractures and the like. In addition, as seen best in FIG. 9, shell 17 includes a distended portion 23 shaped to bend away from the back and bottom of the wearer's heel H so that the wearer's heel is shielded from contact with any potentially ulcer-aggravating materials. Furthermore, as seen best in FIGS. 5 and 6, foot portion 21 is sized to extend beyond the toes T of the wearer to protect the wearer's toes from contact with any potentially ulcer-aggravating items.

As can readily be appreciated, because orthosis 11 is designed to encompass more of a wearer's foot (i.e., total foot contact design) than is typically the case with a multipodus splint, a greater surface area of a wearer's heel and toes can be protected from contact with ulcer-aggravating materials.

Orthosis 11 also includes a reinforcing stay 31 (see FIG. 12 wherein stay 31 is shown separately) fixedly sandwiched between inner layer 15 and outer layer 13 to assist in holding shell 17 in its molded shape. Stay 31 is approximately ⅛ inch in thickness and may be made, for example, from a rigid copolymer plastic. In FIGS. 1–4 and 6–8, the bulges formed in outer layer 13 are caused by stay 31. As can be seen, stay 31 is preferably shaped so as not to be positioned over the wearer's ankle.

Although reinforcing stay 31 is shown in the present embodiment as a unitary structure, it is presently envisioned that stay 31 could be replaced with two or more reinforcing elements.

Figure 5:
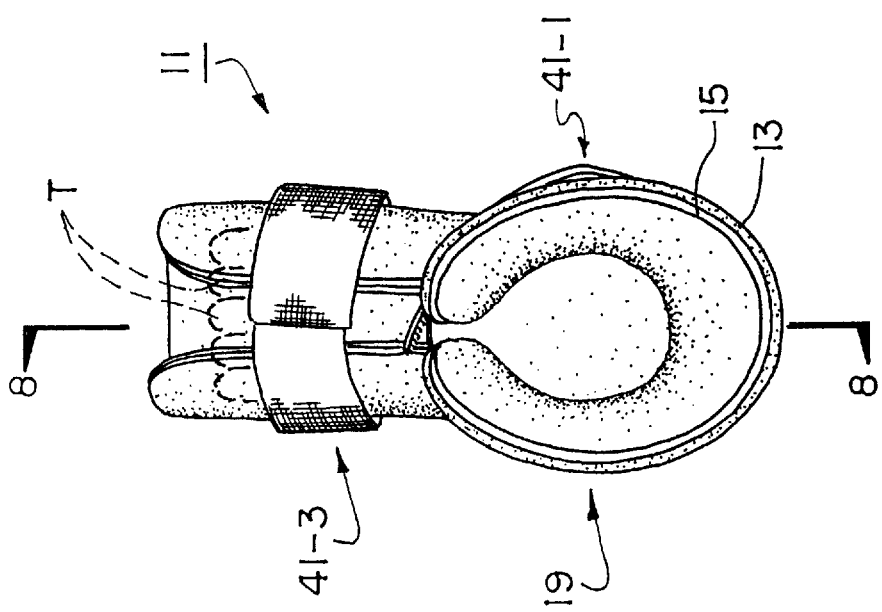
FIG. 5 is a top view of the ankle/foot orthosis shown in FIG. 1, the dotted lines representing in phantom the toes of a person wearing the ankle/foot orthosis.
Figure 8:
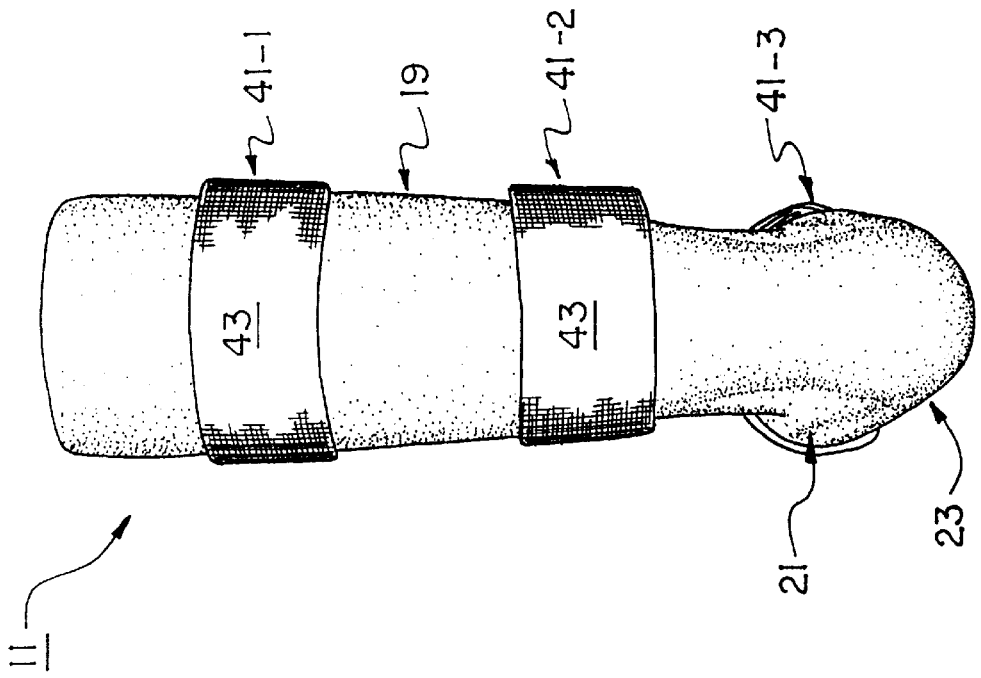
FIG. 8 is a rear view of the ankle/foot orthosis shown in FIG. 1.
Figure 7:
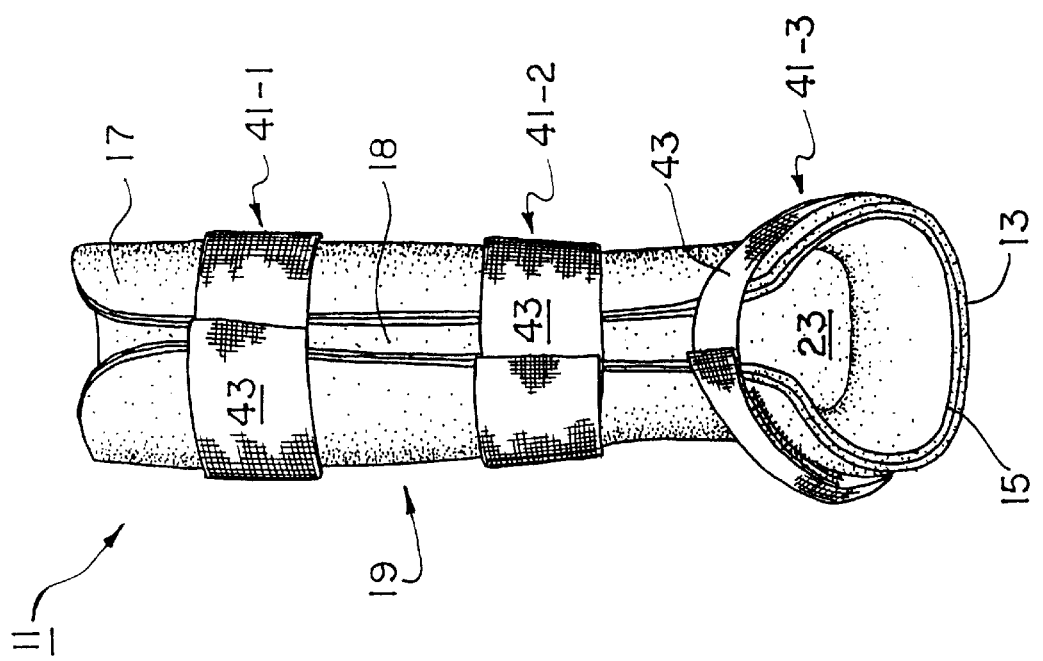
FIG. 7 is a front view of the ankle/foot orthosis shown in FIG. 1.
Figure 11:
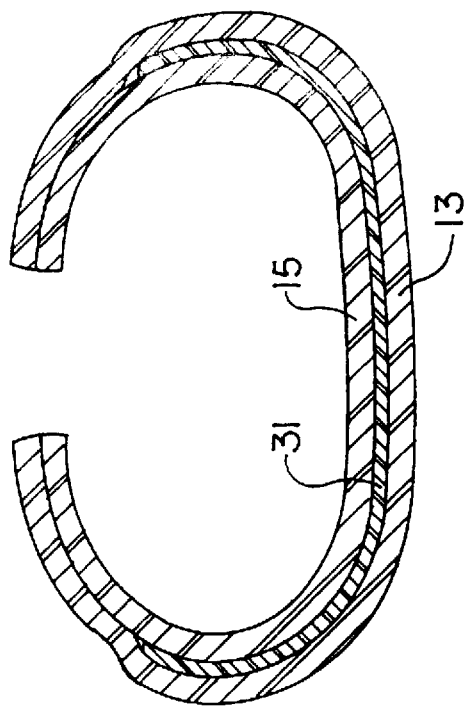
FIG. 11 is a section view of the ankle/foot orthosis of FIG. 1 taken along line 10—10 of FIG. 3.
Figure 10:
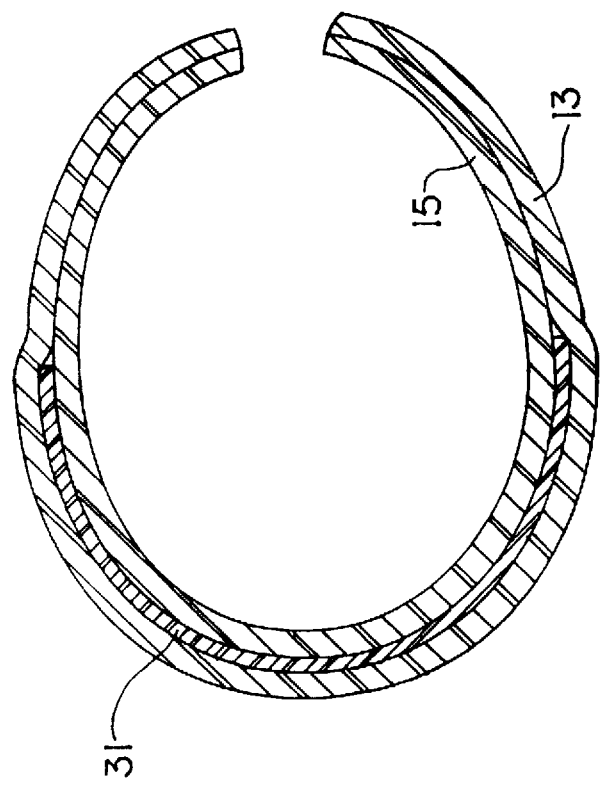
FIG. 10 is a section view of the ankle/foot orthosis of FIG. 1 taken along line 9—9 of FIG. 3, the fastener of the ankle/foot orthosis not being shown for simplicity and clarity.

As can be seen best in FIGS. 2, 5 and 7, shell 17 includes a longitudinally extending split 18 used to facilitate insertion and removal of a patient's leg and foot into and out of orthosis 11. To help hold shell 17 in place on the wearer, orthosis 11 includes a plurality of fasteners 41-1 through 41-3. Each fastener 41 comprises an elongated strip of material 43, one end of which is fixed to shell 17 with a plastic rivet 42 (see FIG. 9) and the other end of which is free to be wrapped transversely across split 18 and around shell 17 (see FIG. 2 wherein the ends of fastener 41-1 are shown unsecured). Hook and loop-type complementary fasteners 47 and 49, respectively, (see FIG. 2) mounted on strip 43 are used to secure the opposite ends of each fastener 41.

The fabrication process for orthosis 11 is more fully described as follows: First, inner layer 15 is formed by heating a ¼ inch thick sheet of soft compressible plastic material of the type described above to a temperature such that it can be shaped as desired. The heated sheet is then wrapped around one of a variety of different sized plaster molds which is equipped with suction (i.e. vacuum means) so that the sheet can be sucked down to conform to the shape of the selected mold. The outer surface of inner layer 15 is then abraded, and stay 31 is placed over the abraded surface. Once stay 31 is in place, adhesive is sprayed over the entire exposed outer surfaces of layer 15 and stay 31. Next, the ¼ inch thick sheet of material used to make outer layer 13 is heated to a temperature such that it can be shaped as desired. The heated sheet is then wrapped around inner layer 15 and stay 31, sucked down by the vacuum to conform to the shape of the mold, allowed to cool and trimmed to shape. Fasteners 41 are then attached to shell 17.

The embodiments of the present invention are intended to be merely exemplary and those skilled in the art shall be able to make numerous variations and modifications to them without departing from the spirit of the present invention. All such variations and modifications are intended to be within the scope of the present invention as defined in the appended claims.

What is claimed is:

1. A soft ankle and foot orthosis comprising:
   (a) an outer layer of soft compressible material;
   (b) an inner layer of soft compressible material, said inner layer of soft compressible material being bonded to the inside of said outer layer of soft compressible material, said inner layer and said outer layer together defining a shell, said shell being sized and shaped to substantially completely surround the lower leg and foot of a person on whom it is to be worn; and
   (c) at least one reinforcing stay sandwiched between said inner layer and said outer layer to assist in holding said shell in its shape.

2. The soft ankle and foot orthosis as claimed in claim 1 wherein each of said inner layer and said outer layer is made from a closed cell polyethylene foam.

3. The soft ankle and foot orthosis as claimed in claim 1 wherein said shell includes a lower leg portion and a foot portion, said lower leg portion and said foot portion being oriented generally perpendicular to one another.

4. The soft ankle and foot orthosis as claimed in claim 1 wherein said shell includes a heel region, said shell being distended in the back and bottom of said heel region so as not to contact the back and bottom of a heel of a person on whom said shell is worn.

5. The soft ankle and foot orthosis as claimed in claim 1 wherein said shell includes a foot portion, said foot portion being sized to extend beyond the toes of a person on whom said shell is worn.

6. The soft ankle and foot orthosis as claimed in claim 1 wherein said shell includes a split for use in facilitating the insertion and removal of a person's foot and leg thereinto and therefrom.

7. The soft ankle and foot orthosis as claimed in claim 6 further comprising a plurality of releasable fasteners used to hold said shell in place on a person on whom said shell is worn.

* * * * *